(12) United States Patent
Biasutti et al.

(10) Patent No.: US 11,590,035 B2
(45) Date of Patent: Feb. 28, 2023

(54) DISPOSABLE ABSORBENT ARTICLES

(71) Applicant: The Procter & Gamble Company, Cincinnati, OH (US)

(72) Inventors: Cagda Biasutti, Frankfurt am Main (DE); Carola Elke Beatrice Krippner, Walkems (DE); Michele Mazzeo, Frankfurt am Main (DE); Henning Roettger, Kaltenkirchen (DE); Reno Volkmer, Pritzwalk (DE)

(73) Assignee: The Procter & Gamble Company, Cincinnati, OH (US)

(*) Notice: Subject to any disclaimer, the term of this patent is extended or adjusted under 35 U.S.C. 154(b) by 596 days.

(21) Appl. No.: 16/412,833

(22) Filed: May 15, 2019

(65) Prior Publication Data

US 2019/0350775 A1   Nov. 21, 2019

(30) Foreign Application Priority Data

May 15, 2018  (EP) .................................. 18172398

(51) Int. Cl.
  *A61F 13/537* (2006.01)
  *A61F 13/15* (2006.01)
  (Continued)

(52) U.S. Cl.
  CPC .. *A61F 13/53743* (2013.01); *A61F 13/15203* (2013.01); *A61L 15/425* (2013.01);
  (Continued)

(58) Field of Classification Search
  CPC .......... A61F 13/537; A61F 2013/53721; A61F 2013/53795; A61F 2013/530007;
  (Continued)

(56) References Cited

U.S. PATENT DOCUMENTS 4,699,619 A   10/1987  Bernardin
5,500,451 A    3/1996  Goldman
(Continued)

FOREIGN PATENT DOCUMENTS

EP   1075241 B1   3/2003
EP   1091714 B1   6/2003
(Continued)

OTHER PUBLICATIONS

CM4989Q PCT International Search Report, dated Aug. 20, 2019, 15 pages.
(Continued)

*Primary Examiner* — Susan S Su
(74) *Attorney, Agent, or Firm* — Amanda Herman Berghauer; Angela K. Haughey

(57) ABSTRACT

An absorbent article including an absorbent core having a fluid distribution layer and fluid storage layer, the fluid distribution layer being formed of two or more sub-layers. A first sub-layer has a first amount of multiple component binder fibers or crosslinked cellulose fibers, or a combination thereof. A second and/or subsequent sub-layer comprises treated or untreated pulp and a second amount of multiple component binder fibers, crosslinked cellulose fibers, or a combination thereof. The % by weight of the first sub-layer of the first amount of multicomponent binder fibers and/or crosslinked cellulose fibers is greater than the % by weight of the second or subsequent sub-layer of the second amount of multiple component binder fibers and/or crosslinked cellulose fibers.

11 Claims, 6 Drawing Sheets

(51) Int. Cl.
*A61L 15/42* (2006.01)
*A61L 15/60* (2006.01)
*A61F 13/53* (2006.01)

(52) U.S. Cl.
CPC ... *A61L 15/60* (2013.01); *A61F 2013/530007* (2013.01); *A61F 2013/530481* (2013.01)

(58) Field of Classification Search
CPC .... A61F 2013/530481; A61F 13/53752; A61F 13/53; A61F 13/53743; A61F 13/53713; A61F 13/53708; A61L 15/425; A61L 15/60
See application file for complete search history.

(56) References Cited

U.S. PATENT DOCUMENTS

| | | | |
|---|---|---|---|
| 5,607,414 | A | 3/1997 | Richards |
| 5,817,704 | A | 10/1998 | Shiveley |
| 5,856,366 | A | 1/1999 | Shiveley |
| 5,869,171 | A | 2/1999 | Shiveley |
| 6,369,121 | B1 | 4/2002 | Catalfamo |
| 6,376,565 | B1 | 4/2002 | Dyer |
| 6,403,857 | B1 | 6/2002 | Gross |
| 6,420,626 | B1 | 7/2002 | Erspamer |
| 6,479,415 | B1 | 11/2002 | Erspamer et al. |
| 6,497,689 | B1 | 12/2002 | Schmidt |
| 6,506,960 | B1 | 1/2003 | Lavon |
| 6,525,106 | B1 | 2/2003 | Desmarais |
| 6,551,295 | B1 | 4/2003 | Schmidt |
| 6,713,661 | B1 | 3/2004 | Arndt |
| 6,727,403 | B1 | 4/2004 | Ehrnsperger |
| 8,629,192 | B2 | 1/2014 | Merrigan |
| 2002/0007169 | A1 | 1/2002 | Graef |
| 2002/0123728 | A1 | 9/2002 | Graef |
| 2003/0135178 | A1* | 7/2003 | Hansen ............... A61F 13/535 604/368 |
| 2004/0176733 | A1* | 9/2004 | Glaug ................. A61F 13/534 604/378 |
| 2007/0118087 | A1 | 5/2007 | Flohr |
| 2010/0262104 | A1 | 10/2010 | Carlucci |
| 2011/0106036 | A1 | 5/2011 | Staahl |
| 2011/0160320 | A1 | 6/2011 | Merrigan |
| 2011/0184365 | A1 | 7/2011 | Roettger |
| 2012/0209233 | A1 | 8/2012 | Steffen et al. |
| 2015/0164710 | A1 | 6/2015 | Ehkme |

FOREIGN PATENT DOCUMENTS

| | | |
|---|---|---|
| EP | 1061878 B1 | 11/2004 |
| WO | WO99063923 A1 | 12/1999 |
| WO | WO2000/000138 A1 | 1/2000 |
| WO | WO2000074620 A1 | 12/2000 |
| WO | WO2003/090656 A1 | 11/2003 |
| WO | WO2007/069964 A1 | 6/2007 |
| WO | WO2007069964 A1 | 6/2007 |
| WO | WO2010118272 | 10/2010 |
| WO | WO2011/084981 A1 | 7/2011 |
| WO | WO2011081987 A1 | 7/2011 |
| WO | 2011092025 A1 | 8/2011 |
| WO | WO2014/009506 A1 | 1/2014 |
| WO | WO2015187789 A1 | 12/2015 |
| WO | WO2016/040097 A1 | 3/2016 |

OTHER PUBLICATIONS

CM4990Q PCT International Search Report, dated Aug. 20, 2019, 13 pages.
CM4989Q European Search Report, dated Nov. 23, 2018, 8 pages.
CM4990Q European Search Report, dated Oct. 25, 2018, 8 pages.

* cited by examiner

Cross Section A-A

Cross Section B-B

DISPOSABLE ABSORBENT ARTICLES

FIELD OF THE INVENTION

The present disclosure generally relates to a disposable absorbent article having an absorbent core comprising a fluid distribution layer and a fluid storage layer.

BACKGROUND OF THE INVENTION

Disposable absorbent articles such as feminine hygiene products, taped diapers, pant-type diapers and incontinence products are designed to absorb fluids from the wearer's body. Users of such disposable absorbent articles have several concerns. Leakage from products like catamenial pads, diapers, sanitary napkins, and incontinence pads is a significant concern. Comfort and the feel of the product against the wearer's body is also a concern. To provide better comfort, current disposable articles are typically provided with a topsheet that is flexible, soft feeling, and non-irritating to the wearer's skin. The topsheet does not itself hold the discharged fluid. Instead, the topsheet is fluid-permeable to allow the fluids to flow into an absorbent core.

Current disposable articles are also provided with an absorbent core, also referred to as an absorbent system, typically comprising an acquisition and/or fluid distribution layer and a fluid storage layer. The fluid distribution layer is typically placed on top of the body facing surface of the fluid storage layer and has the function of rapidly acquiring fluids excreted from the body and transferring them rapidly away from the body into the fluid storage layer. The fluid distribution layer is also used to keep exudates held in the fluid storage layer away from the skin surface during use and/or as pressure is applied to the article. This leads to a constant trade-off between effectiveness of a fluid distribution layer to draw liquid away from the surface, while still providing a comfortable and dry absorbent article.

The present invention seeks to further improve this trade-off between comfort and effectiveness in an absorbent article by providing a specifically designed absorbent core to ensure effective absorption while providing a more pleasant consumer experience.

SUMMARY OF THE INVENTION

The present invention relates to an absorbent article having a topsheet, backsheet and absorbent core. The absorbent core has a fluid distribution layer, adjacent the topsheet and a fluid storage layer between the fluid distribution layer and the backsheet. The fluid distribution layer is formed of two or more sub-layers, the first sub-layer proximal to the topsheet having a first amount of multiple component binder fibers or crosslinked cellulose fibers, or a combination thereof. A second and/or subsequent sub-layer distal from the topsheet comprises treated or untreated pulp and a second amount of multiple component binder fibers, crosslinked cellulose fibers, or a combination thereof. The % by weight of the first sub-layer of the first amount of multicomponent binder fibers and/or crosslinked cellulose fibers is greater than the % by weight of the second or subsequent sub-layer of the second amount of multiple component binder fibers and/or crosslinked cellulose fibers. Furthermore, the fluid storage layer has at least 50% by weight of the fluid storage layer of a super absorbent polymer.

The fluid distribution layer is configured to quickly acquire liquid from the topsheet, drawing it deep into the fluid distribution layer until such time that the liquid is absorbed by the fluid storage layer. By providing a greater % by weight of the layer of multicomponent binder fibers and/or crosslinked cellulose fibers in the first sub-layer compared with the second and/or subsequent layer provides a fluid distribution layer with a relatively more open structure in an area proximal to the topsheet. The open structure enables quick acquisition of liquid from the top sheet and has good recovery properties after liquid has been drawn down through the second sub-layer and into the fluid storage layer. The second and/or subsequent sub-layer balances the need to draw liquid from the topsheet and to retain it until absorption by the fluid storage layer, thereby preventing rewet during use of such an absorbent article.

Figure 1:
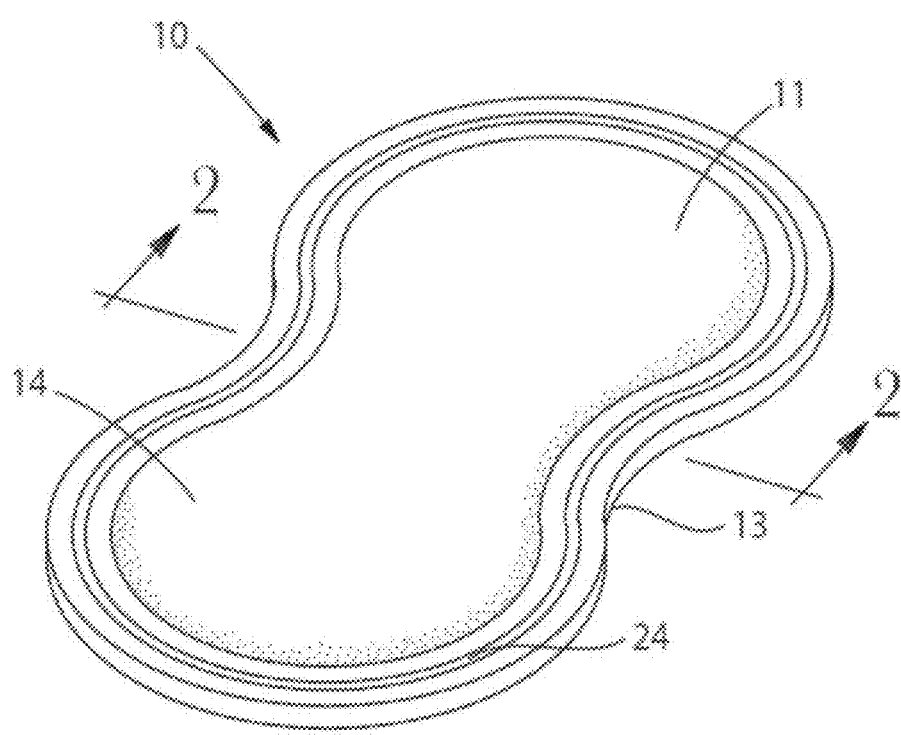
FIG. 1 is a perspective view of one example of an absorbent article that incorporates an absorbent core.

While the specification concludes with claims particularly pointing out and distinctly claiming the subject matter that is regarded as the present invention, it is believed that the invention will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. The drawings are not necessarily to scale.

DETAILED DESCRIPTION

As used herein, the following terms shall have the meaning specified thereafter:

All percentages are to be considered as weight percentages unless otherwise specified.

"Absorbent article" refers to wearable devices, which absorb and/or contain liquid, and more specifically, refers to devices, which are placed against or in proximity to the body of the wearer to absorb and contain the various exudates discharged from the body, such as menses or urine. Absorbent articles can include diapers, training pants, adult incontinence undergarments (e.g., liners, pads and briefs) and/or feminine hygiene products.

The "longitudinal" direction is a direction running parallel to the maximum linear dimension, typically the longitudinal axis, of the article and includes directions within 45° of the longitudinal direction. "Length" of the article or component thereof, when used herein, generally refers to the size/distance of the maximum linear dimension, or typically to the size/distance of the longitudinal axis, of an article or part thereof.

The "lateral" or "transverse" direction is orthogonal to the longitudinal direction, i.e., in the same plane as the majority of the article and the longitudinal axis, and the transverse direction is parallel to the transverse axis. "Width" of the article or of a component thereof, when used herein, refers to the size/distance of the dimension orthogonal to the longitudinal direction of the article or component thereof, i.e., orthogonal to the length of the article or component thereof, and typically it refers to the distance/size of the dimension parallel of the transverse axis of the article or component.

The "Z-direction", or "thickness" is orthogonal to both the longitudinal and transverse directions and typically extends from the upper body-facing surface of the absorbent article to the lower garment-facing surface.

"Machine Direction" or "MD" as used herein means the direction parallel to the flow of a manufacturing machine, such as the airlaid making machine and/or absorbent article product manufacturing equipment.

"Cross Machine Direction" or "CD" as used herein means the direction parallel to the width of the manufacturing machine, for example an airlaid making machine and/or absorbent article product manufacturing equipment and perpendicular to the machine direction.

The terms "upper", "upward" or corresponding expressions refer z-directionally to a direction or relative orientation or positioning of an absorbent article or its components when in use as positioned or worn by a user and relative to the user's body. Thus, a topsheet of an absorbent article may be positioned as the most outward layer of the article and its outer surface may be intended for contact with the skin of a wearer. Accordingly, the absorbent article may exhibit "upper" elements or surfaces that are positioned relative to other "lower" elements or components that are positioned further away from a user's skin during use.

Likewise, the terms "lower", "downwards" or corresponding expressions refer z-directionally to a direction or relative orientation or positioning of an absorbent article or its components when in use as positioned or worn by a user and relative to the user's body. Typically, a backsheet of an absorbent article may be positioned as the outermost layer of the article and its outer surface may be intended to be in contact with the garment of a wearer.

"Absorbent core" or "absorbent system" refers to a structure typically disposed between a topsheet and backsheet of an absorbent article for absorbing and containing liquid received by the absorbent article. In the present invention, the absorbent core includes at least a fluid distribution (or fluid acquisition) layer and fluid storage layer, however it will be appreciated that the absorbent core may include other layers that are positioned between the topsheet and backsheet.

As used herein, the term "foam" is synonymous with the term "cellular polymer" which includes materials having a significant void volume, typically greater than 75%. "Open-celled" foams further have a reticulated internal structure disposed therein comprising relatively thin "strut" elements interconnected and forming cells or pores providing for fluid communication throughout the structure. Mean cell diameters refer to the diameter of the pores in the foam visible by microscopy. The pores tend to be relatively spherical in shape and the mean diameter can be measured by using microscopic techniques. One suitable technique is to use a scanning electron micrograph and measure the apparent mean diameter of at least 25 representative cells to determine the mean. The density of foams can be determined using uncompressed samples of said foams devoid of contaminants such as water, and measuring the volume and weight of the foam. A cubic sample having an edge length greater than or equal to 2 cm is practical.

In all cases, when describing the absorbent article and the absorbent core of the present invention, it is considered that the article and the absorbent structure are in a flattened configuration where the plane of the article is the x,y plane and the z axis is perpendicular to said plane.

The term "treated pulp" is equivalent to "softener treated pulp" and to "debonder treated pulp", all of which refer to fluff pulp treated with debonding agents which reduce the strength of hydrogen bonding between cellulose molecules.

"Nonwoven material" refers to a manufactured web of directionally or randomly oriented fibers, excluding paper and products which are woven, knitted, tufted, stitch-bonded incorporating binding yarns or filaments, or felted by wet-milling, whether or not additionally needled. Nonwoven materials and processes for making them are known in the art. Generally, processes for making nonwoven materials comprise laying fibers onto a forming surface, which can comprise spunlaying, meltblowing, carding, airlaying, wet-laying, coform and combinations thereof. The fibers can be of natural or man-made origin and may be staple fibers or continuous filaments or be formed in situ.

The term "hydrophilic" describes fibers or surfaces of fibers, which are wettable by aqueous fluids (e.g., aqueous body fluids) deposited on these fibers. Hydrophilicity and wettability are typically defined in terms of contact angle and the surface tension of fluids as they pass through a material. A fiber or surface of a fiber is said to be wetted by an aqueous fluid (i.e., hydrophilic) when either the contact angle between the fluid and the fiber, or its surface, is less than 90 degrees, or when the fluid tends to spread spontaneously across the surface of the fiber. Conversely, a fiber or surface of the fiber is considered to be "hydrophobic" if the contact angle is greater than 90 degrees and the fluid does not spread spontaneously across the surface of the fiber.

Absorbent Article

A disposable absorbent article as disclosed herein may take a variety of different forms, such as diapers, feminine hygiene products and incontinence products such as sanitary napkins and incontinence pads. One non-limiting embodiment of a disposable absorbent article as detailed herein is shown as a sanitary napkin in FIGS. 1 and 2. For the purposes of this application, a sanitary napkin will be specifically illustrated and described, although any features or elements of the sanitary napkin that are disclosed are also contemplated for any other embodiment of absorbent article, including incontinence pads.

A sanitary napkin 10 can have any shape known in the art for feminine hygiene articles, including the generally symmetric "hourglass" shape shown in FIG. 1, as well as pear shapes, ovals, oblong ovals, droplet shapes, bicycle-seat shapes, trapezoidal shapes, or wedge shapes. Sanitary napkins and pantiliners can also be provided with lateral extensions known in the art as "flaps" or "wings" (not shown in FIG. 1). Such extensions can serve a number of purposes, including, but not limited to, protecting the wearer's panties from soiling and keeping the sanitary napkin secured in place. The illustrated absorbent article has a body-facing upper side that contacts the user's body during use. The opposite, garment-facing lower side contacts the user's clothing during use.

Figure 2A:
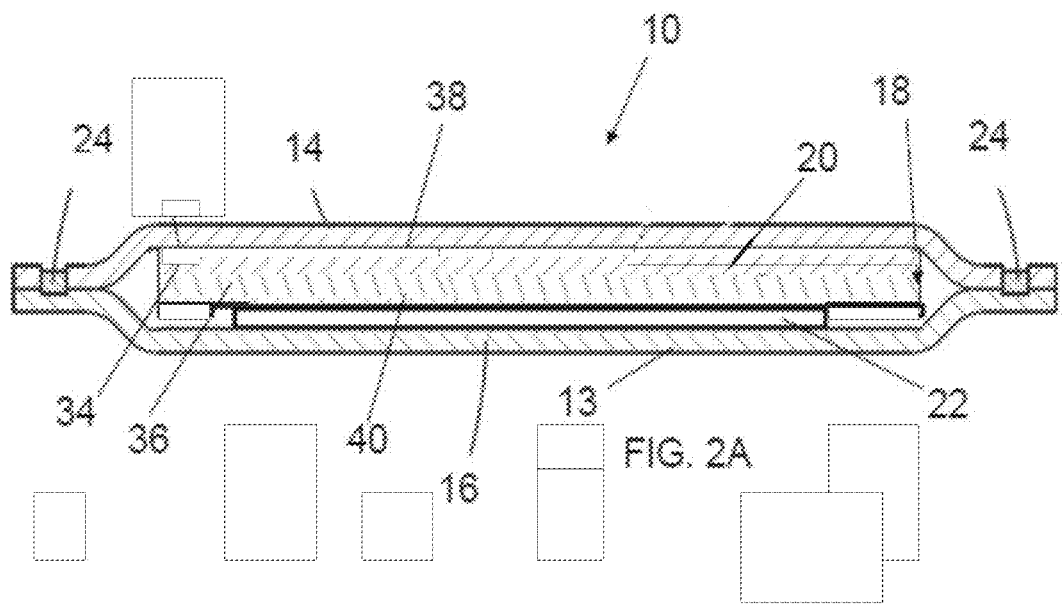
FIGS. 2A and 2B are representative cross-sectional views of the absorbent article of FIG. 1 taken through line 2-2.
Figure 2B:
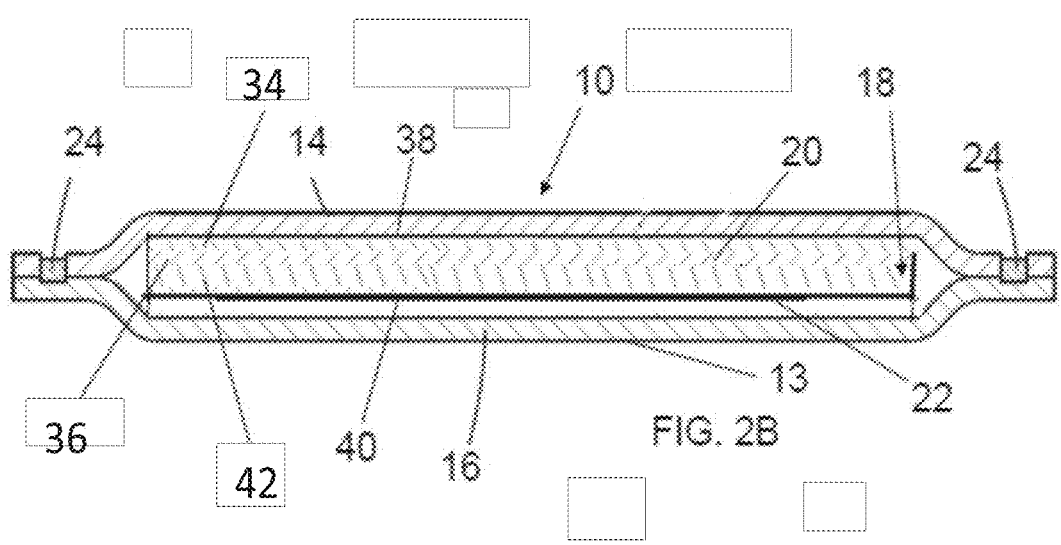
Figure 3:
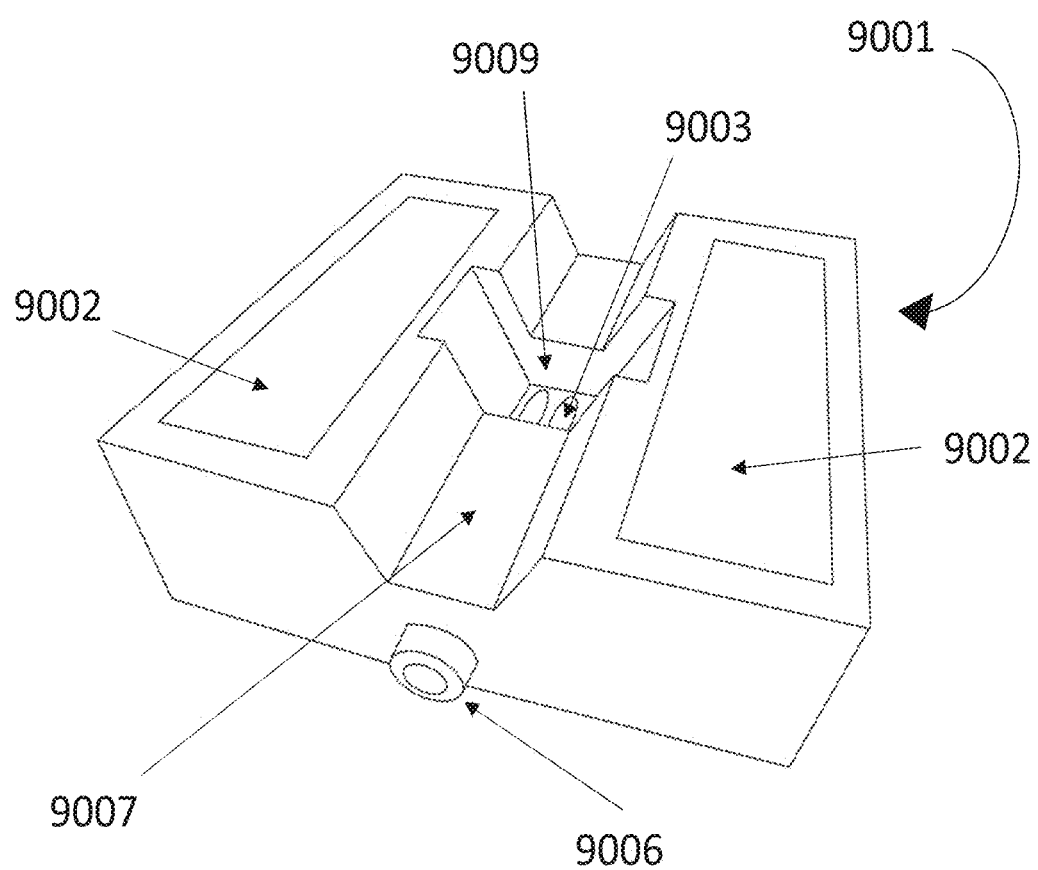
FIGS. 3, 4A, 4B, 5A and 5B are schematic representations of the equipment used to measure Multiple Strike Through and End Rewet.
Figure 4A:
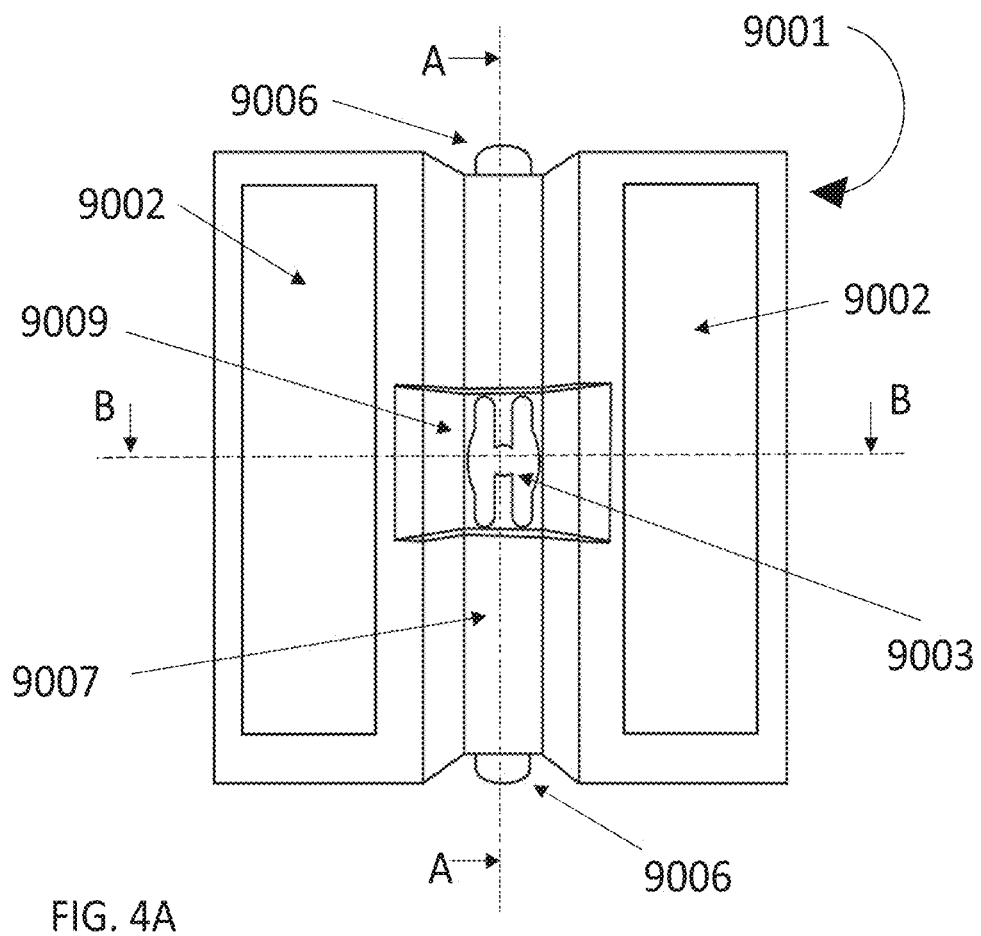
Figure 4B:
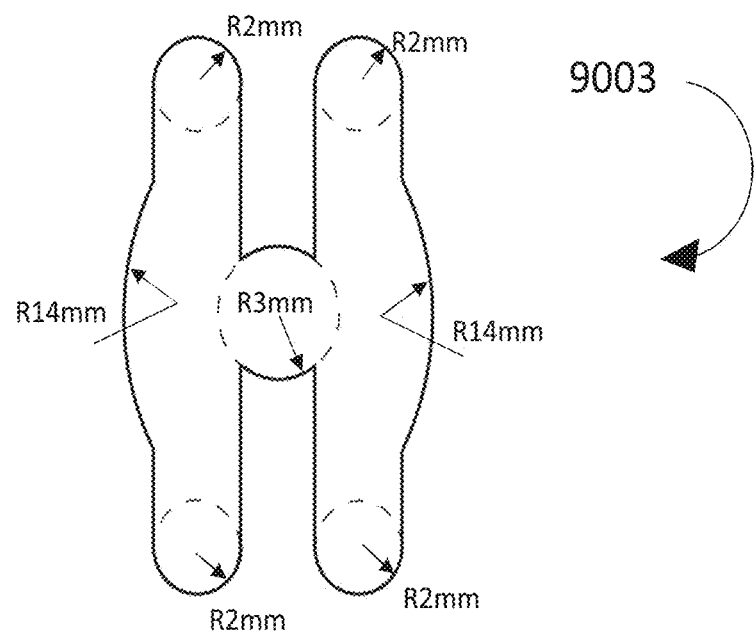
Figure 5A:
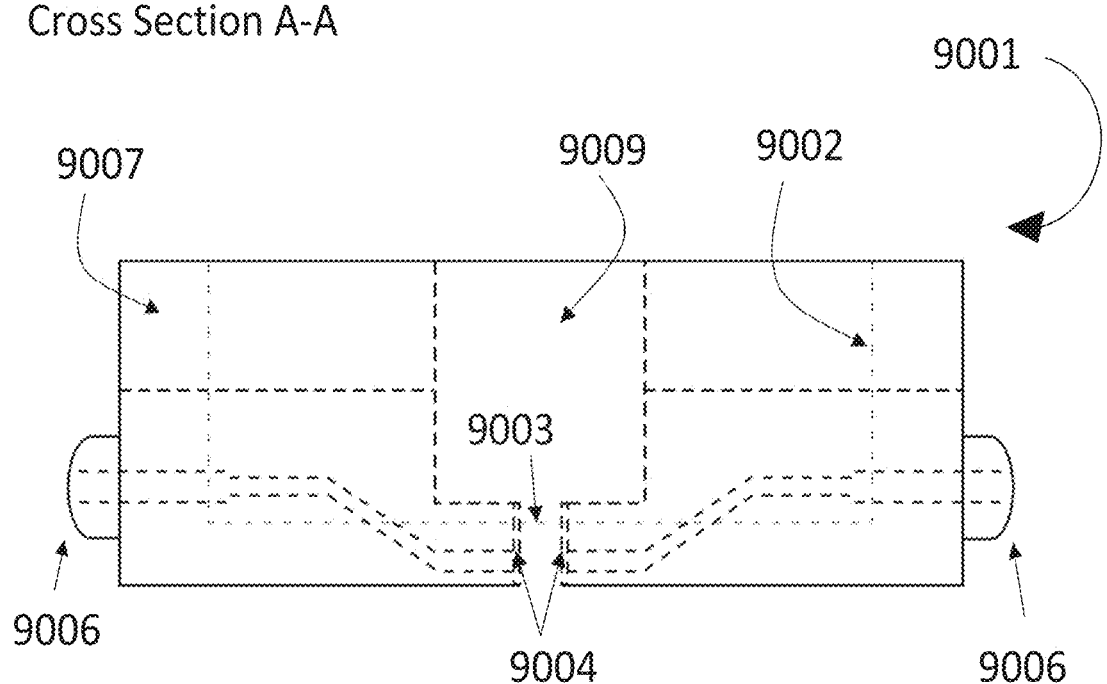
Figure 5B:
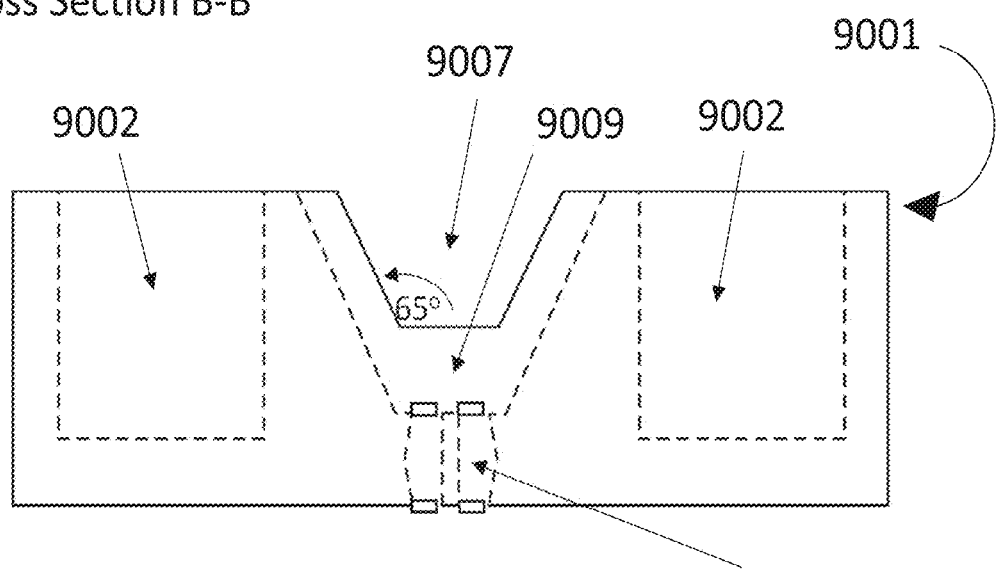

The upper side of the sanitary napkin 10 generally has a topsheet 14 that can be liquid pervious. The lower side (seen in FIGS. 2A and 2B) has a backsheet 16 that is often liquid impervious and is joined with the topsheet 14 at the edges of the sanitary napkin 10. The backsheet and the topsheet may be secured together in a variety of ways, for example with adhesive, heat bonding, pressure bonding, ultrasonic bonding, dynamic mechanical bonding, a crimp seal, or by any other suitable securing method. As shown in FIG. 2, a fluid impermeable crimp seal 24 can resist lateral migration ("wicking") of fluid through the edges of the product, inhibiting side soiling of the wearer's undergarments.

As is typical for sanitary napkins and the like, the sanitary napkin 10 of the present disclosure can have panty-fastening adhesive disposed on the garment-facing side of the backsheet 16. The panty-fastening adhesive can be any of known adhesives used in the art for this purpose, and can be covered prior to use by a release paper, as is well known in the art. If flaps or wings are present, a panty fastening adhesive can be applied to the garment facing side so as to contact and adhere to the underside of the wearer's panties.

An absorbent core 18 is positioned between the topsheet 14 and the backsheet 16. The illustrated sanitary napkin 10 has a body-facing upper side 11 that contacts the user's body during use. The opposite, garment-facing lower side 13 contacts the user's clothing during use. As shown in FIG. 2A, the absorbent core 18 may include a fluid distribution layer 20 for drawing liquid into the sanitary napkin from the topsheet and a fluid storage layer 22 where exudates are eventually held.

The topsheet 14 and the backsheet 16 may be joined directly to each other in the periphery of the sanitary napkin or they may be indirectly joined together by directly joining them to the absorbent core 18 or additional optional layers within the chassis, such as a secondary topsheet.

Topsheet

The absorbent article may comprise any known or otherwise effective topsheet, such as one which is compliant, soft feeling, and non-irritating to the wearer's skin. Suitable topsheet materials include a liquid pervious material that is oriented towards and contacts the body of the wearer permitting bodily discharges to rapidly penetrate through it without allowing fluid to flow back through the topsheet to the skin of the wearer. A suitable topsheet can be made of various materials such as woven and nonwoven materials; aperture film materials including aperture formed thermoplastic films, aperture plastic films, and fiber-entangled aperture films; hydro-formed thermoplastic films; porous foams; reticulated foams; reticulated thermoplastic films; thermoplastic scrims; or combinations thereof. Suitable woven and nonwoven materials can comprise natural fibers (e.g., wood or cotton fibers), synthetic fibers (e.g., polymeric fibers such as polyester, polypropylene, or polyethylene fibers) or from a combination of natural and synthetic fibers. When the topsheet comprises a nonwoven web, the web may be manufactured by a wide number of known techniques. For example, the web may be spunbonded, carded, wet-laid, melt-blown, hydroentangled, combinations of the above, or the like. Suitable nonwoven materials may include low basis weight nonwovens, that is, nonwovens having a basis weight of from about 8 g/m$^2$ to about 25 g/m$^2$.

Topsheets may be formed by one or more of the layers made of the materials mentioned above, where one layer forms the outer surface of the absorbent article and one or more other layers are positioned immediately below it. The layer forming the outer surface of the article is typically a nonwoven layer or a formed film and it can be treated to be hydrophilic using surfactants or other means known to the person skilled in the art. Topsheets may additionally be apertured, have any suitable three-dimensional feature and/ or have a plurality of embossments (e.g., a bond pattern). The topsheet may additionally be provided with tufts, formed with a laminated topsheet having an apertured upper layer and nonwoven lower layer, with "tufts" formed from the nonwoven layer protruding through the apertured upper layer.

Backsheet

The backsheet acts as a barrier to any absorbed bodily fluids that may pass through the absorbent core to the garment surface thereof with a resulting reduction in risk of staining undergarments or other clothing. Further, the barrier properties of the backsheet permit manual removal, if a wearer so desires, of the absorbent article with reduced risk of hand soiling. The backsheet may be positioned adjacent a garment-facing surface of the absorbent core and may be joined thereto by attachment methods (not shown) such as those well known in the art. For example, the backsheet may be secured to the absorbent core by a uniform continuous layer of adhesive, a patterned layer of adhesive, or an array of separate lines, spirals, or spots of adhesive. Alternatively, the attachment methods may comprise using heat bonds, pressure bonds, ultrasonic bonds, dynamic mechanical bonds, or any other suitable attachment methods or combinations of attachment methods. Forms of the present disclosure are also contemplated wherein the absorbent core is not joined to the backsheet, the topsheet or both.

The backsheet may be impervious, or substantially impervious, to liquids (e.g., menses or urine) and may be manufactured from a thin plastic film, although other flexible liquid impervious materials may also be used. As used herein, the term "flexible" refers to materials which are compliant and will readily conform to the general shape and contours of the human body. The backsheet may prevent, or at least inhibit, the exudates absorbed and contained in the absorbent core from wetting articles of clothing which contact the absorbent article such as undergarments. However, in some instances, the backsheet may permit vapors to escape from the absorbent core (i.e., it is breathable) while in other instances the backsheet may not permit vapors to escape (i.e., non-breathable). Thus, the backsheet may comprise a polymeric film such as thermoplastic films of polyethylene or polypropylene. A suitable material for the backsheet is a thermoplastic film having a thickness of from about 0.012 mm to about 0.051 mm, for example.

Another suitable backsheet material is a polyethylene film having a thickness of from about 0.012 mm to about 0.051 mm. The backsheet may be embossed and/or matte finished to provide a more clothlike appearance. For a stretchable but non-elastic breathable (i.e., permeable to water vapour and other gases) backsheet, a hydrophobic, stretchable, spun laced, non-woven material having a basis weight of from about 30 g/m$^2$ to 40 g/m$^2$, formed of polyethylene terephthalate or polypropylene fibers may be used. Other suitable breathable backsheets for use herein include single layer breathable backsheets which may be breathable and liquid impervious, and backsheets formed of two or more layers which in combination provide breathability and liquid imperviousness. For example, the backsheet may have a first layer comprising a gas permeable aperture formed film layer and a second layer comprising a breathable microporous film layer.

Where the backsheet is formed of a nonwoven web, it may have a basis weight of between 20 g/m$^2$ and 50 g/m$^2$.

Absorbent Core

Referring to FIG. 1, the absorbent core 18 is configured to store bodily fluids discharged during use. The absorbent core 18 may be manufactured in a wide variety of sizes and shapes, and may be profiled to have different thickness, hydrophilic gradients, superabsorbent gradients, densities, or average basis weights at different x-y-directional positions across the face of the sanitary napkin 10. As shown in FIGS. 2A and 2B, the absorbent core comprises a fluid distribution layer 20 and a storage layer 22. The fluid distribution layer is configured to transfer the received fluid both downwardly and laterally, and generally has a higher permeability than the storage layer.

Fluid Distribution Layer

The fluid distribution layer is configured to acquire fluids from the topsheet and store the fluid until such time that it can be absorbed by the fluid storage layer. It is important that liquid held in the fluid distribution layer does not transfer back to the topsheet (rewet). The fluid distribution layer may have the same or similar shape and size as the topsheet and overall absorbent article, or it may be smaller. In general, a well-functioning fluid distribution layer contributes considerably to the comfort experienced by a user and, as such, aims at balancing the trade-off between the speed with which fluid is acquired by the fluid distribution layer, the possibility of rewet and the level of comfort provided to a user.

The fluid distribution layer has a structure that enables it to receive and draw liquid from the topsheet, to hold the liquid and to prevent rewet (e.g., through a topsheet), while still allowing the liquid to be drawn out by the fluid storage layer. To address this, the fluid distribution layer may comprise two or more sub-layers 34, 36, 42 having differing properties. In this respect, it has been found that to draw liquid down and away from the topsheet, the fluid distribution layer needs to have a certain permeability—that can be provided with a generally open structure formed from fibers making up the fluid distribution layers. However, the present inventors have realised that providing a wholly open structure can result in problems of rewet during use and, or it may lack the capillary action required to draw liquid away from the topsheet in the first place.

The fluid distribution layer has a first body facing surface 38 and a second garment facing surface 40 and is formed of two or more sub-layers having different material properties. The first sub-layer 34 forms or is adjacent to the body facing surface of the fluid distribution layer (proximal to the topsheet). One or more additional sub-layers may be provided. For example, a second sub-layer 36 is provided that forms or is adjacent to the garment facing surface of the fluid distribution layer. Alternatively, a third sub-layer 42 (shown in FIG. 2B) could be provided adjacent the garment facing surface of the fluid distribution layer, in which case the second sub-layer is positioned between the first and third sub-layer. The ratio of fibers in the different sub-layers may be different, but once integrated, the sub-layers form one heterogeneous structure that cannot be easily separated.

To ensure rapid acquisition of fluid but minimal rewet, it is necessary for the first sub-layer to be able to quickly draw liquid down from the topsheet and to allow the liquid to pass through to the second (or more) sub-layer that is further away from the topsheet. The first sub-layer should also be capable of quickly recovering form to ensure that the user does not experience a long period of discomfort as a result of the fluid distribution layer having become wet. To ensure the liquid is then held away from the topsheet, the second or subsequent sub-layers are required to continue to draw liquid away from the topsheet and first sub-layer, but to hold the liquid until such time as it is absorbed by the storage layer.

Sub-layers of the fluid distribution layer may be formed of a combination of pulp fibers and/or cross-linked cellulose fibers and/or bicomponent binder fibers and, dependent on the manufacturing process, optionally dispersion binder. The first sub-layer, located on the body-facing side of the fluid distribution layer, has a more open, i.e., less dense and more permeable, structure than the second or subsequent layers. Thus, it is possible for the first sub-layer to quickly draw liquid into the absorbent core. The first sub-layer may comprise crosslinked cellulose fibers or a combination of multi-component fibers and crosslinked cellulose fibers and/or pulp fibers. Where the first sub-layer contains only fibers (e.g. crosslinked cellulose or crosslinked cellulose and pulp fibers), the second and/or subsequent layers of the fluid distribution layer will comprise multi-component fibers. The presence of multi-component fibers in any part of the fluid distribution layer helps to ensure integrity of the fluid distribution layer as, upon heating, the multicomponent fibers form a self-adhering structure.

Use of crosslinked fibers or multi-component binder fibers in combination with crosslinked or pulp fibers in the first sub-layer has been found to provide an open structure that allows quick acquisition of liquid from the top sheet and has good recovery properties after liquid has been removed from the fluid distribution layer by the fluid storage layer. Both factors contribute significantly to comfort experienced by a user both in wet and dry conditions.

The first sub-layer may comprise from 50%, 60%, 70%, 80% or 90% by weight of the first sub-layer of a first amount of crosslinked cellulose fibers, optionally comprising additional multicomponent binder fibers, pulp fibers and/or dispersion binders. Alternatively, the first sub-layer may comprise from 25% to 75%, 30% to 70% or 40% to 60% by weight of the first sub-layer of multicomponent fibers, together with cross-linked or pulp fibers and optionally dispersion binders. Alternatively, the first sub-layer may comprise from 25% to 100% by weight of the first sub-layer of crosslinked cellulose fibers or pulp fibers and from 0% to 75% by weight of the first sub-layer of multicomponent fibers or 40% to 100% by weight of the first sub-layer of crosslinked cellulose fibers or pulp fibers and from 0% to 60% by weight of the first sub-layer of multicomponent fibers. Preferably, the second sub-layer may comprise a second amount of crosslinked cellulose fibers and/or multi-component binder fibers where the % by weight of the second sub-layer of the second amount is less than the first amount. Subsequent sub-layers may comprise the same or less % by weight of each subsequent sub-layer than the second amount of crosslinked and/or multicomponent binder fibers. Preferably, the second and any subsequent sub-layers comprise less than 70%, 60%, 50%, 30% or 10% by weight of the respective sub-layer of cross-linked and/or multicomponent binder fibers as the first amount of cross-linked cellulose or multicomponent fibers in the first sub-layer.

Preferably, the first sub-layer comprises from 50% to 70% by weight of the first sub-layer of multicomponent binder fibers and from 30% to 50% by weight of the first sub-layer of crosslinked cellulose or pulp fibers and the second sub-layer comprises less than 20% by weight of the second sub-layer of multicomponent binder and/or crosslinked cellulose fibers. In an alternative preferred embodiment, the first sub-layer comprises from 25% to 100% of crosslinked cellulose fibers and from 5% to 75% by weight of the first sub-layer of multicomponent fibers and the second sub-layer comprises less than 20% by weight of the second sub-layer of multicomponent binder and/or crosslinked cellulose fibers.

Without being bound by theory, the multicomponent binder fibers enhance structural integrity of the fluid distribution layer while also providing for a more open structure.

The crosslinked cellulose fibers provide liquid storage capability and provide a springy open structure that enables quick recovery of the fluid distribution layer to enable readiness for multiple assaults. Use of a first amount of multicomponent fibers or crosslinked cellulose fibers in the first sub-layer that is greater than the second or subsequent amounts of multicomponent fibers and/or crosslinked cellulose fibers in the second or subsequent sub-layers has been found to provide the benefits discussed above. However, in an embodiment, the first sub-layer comprises a first amount of cross-linked fibers and multicomponent fibers.

The second and subsequent sub-layers comprise treated or untreated pulp and may additionally comprise multicomponent binder fibers, crosslinked cellulose fibers or a dispersion binder, such as latex, or a combination thereof. Preferably, the second and subsequent sub-layers comprise no more than 50% by weight of the total fluid distribution layer of crosslinked cellulose fibers or multicomponent binder fibers.

Preferably, the first sub-layer has a % weight of the fluid distribution layer of between 20% to 60%. If the first sub-layer has a % weight of less than 20%, it is expected that the acquisition of time of liquids from the topsheet will increase and comfort levels will decrease. By contrast, if the weight ratio of first sub-layer to second or subsequent sub-layers is too great, then the open structure of the first sub-layer may not provide sufficient suction force to draw liquids away from liquid receiving surface and/or the topsheet.

Multicomponent binder fibers can be formed, for example, by polyethylene and polypropylene, polyethylene/polyethylene terephthalate, metallocene PP with PET core, and can have any configuration known in the art such as for example core-sheath, star, fiber eccentric, fiber concentric, side by side and a mixture thereof.

Often, an absorbent article, when being worn, is exposed to a certain pressure exerted by the wearer, which potentially decreases the void space in the fluid distribution member. Having good permeability and sufficient void space available is important for good liquid distribution and transport. It is further believed that the bi-component fibers and cross-linked cellulose fibers described above are suitable to maintain sufficient void volume even when a fluid distribution layer is exposed to pressure.

The remaining fibers may be selected from natural, regenerated and synthetic fibers. In order to improve wettability, it is preferred that at least 90% weight of the fibers (or in some embodiments, 100% wt) are hydrophilic or are hydrophilically treated (e.g., with a surfactant) so as to exhibit hydrophilic properties. The multicomponent binder fibers may also be treated to exhibit hydrophilic properties.

Examples of fibers suitable for use in the fluid distribution layer (in addition to the multicomponent binder fibers) are synthetic or regenerated fibers selected from PET, polyethylene, polypropylene, nylon, rayon, pulp, polylactic acid and mixtures thereof.

In addition to the materials described above, the fluid distribution layer can comprise a wide variety of liquid-absorbent materials commonly used in disposable absorbent articles. Non-limiting examples of liquid-absorbent materials suitable for use include comminuted wood pulp which is generally referred to as airfelt or pulp; creped cellulose wadding; chemically stiffened, modified, or cross-linked cellulose fibers, cotton fibers; meltblown polymers including co-form; synthetic fibers including crimped polyester fibers; capillary channel fibers; absorbent foams; absorbent sponges; synthetic staple fibers.

The fluid distribution layer may be formed as a unitary structure—meaning that although it may be formed by several sub-layers that have distinct properties and/or compositions from one another, they are somehow intermixed at the boundary region so that, instead of a definite boundary between sub-layers, it would be possible to identify a region where the different sub-layers transition one into the other. Such a unitary structure is typically built by forming the various sub-layers one on top of the other in a continuous manner, for example using air laid or wet laid deposition. Typically, there is no adhesive used between the sub-layers of the unitary material. However, in some cases, adhesives and/or binders can be present although typically in a lower amount that in multilayer materials formed by separate layers.

In an embodiment, the fluid distribution layer may comprise a fibrous nonwoven layer comprising fibers having an average length from 25 mm to 200 mm, 50 mm to 175 mm or 75 mm to 125 mm. In some embodiments, the average fiber size in dtex can be selected so as to be in the range of from 0.5 dtex to 15 dtex, 1 dtex to 12.5 dtex, 3 dtex to 10 dtex or 5 dtex to 7.5 dtex. The average fiber length is measured according to ASTM method D5103-07 and the average size in dtex according to the ASTM method D1577-07. The nonwoven layer forming the unitary fluid distribution layer can have a basis weight of from 10 $g/m^2$ to 50 $g/m^2$, 15 $g/m^2$ to 40 $g/m^2$, 20 $g/m^2$ to 30 $g/m^2$ and a thickness from 0.2 mm to 5 mm, 0.5 mm to 4 mm, or 1 mm to 3 mm and can be selected from needlepunched, hydroentangled, air through bonded, spunbonded, carded resin bonded, and melt blown nonwoven materials. Air through carded nonwovens are in some cases preferred because this consolidation technology can result in materials having a good z-direction compression resistance, and good capillarity even at low basis weight (thus allowing to manufacture thinner and lower cost absorbent elements).

The nonwoven layer of the fluid distribution layer can be manufactured from an assortment of suitable fiber types that produce the desired mechanical performance and fluid handling performance. In some embodiments, an air through bonded carded nonwoven may be formed from a combination of stiffening fibers. The stiffening fibers, for example, can form about 20% to about 40%, by weight, of the air through carded fiber nonwoven. In other embodiments, the stiffening fibers can form about 100%, by weight, of the nonwoven.

The stiffening fibers can be polyethylene terephthalate (PET) fibers, or other suitable non-cellulosic fibers known in the art. The PET fibers can have any suitable structure or shape. For example, the PET fibers can be round or have other shapes, such as spiral, scalloped oval, trilobal, scalloped ribbon, and so forth. Further, the PET fibers can be solid, hollow or multi-hollow. In some embodiments of the carded fiber nonwoven, the stiffening fibers may be fibers made of hollow/spiral PET. Other suitable examples of stiffening fibers include polyester/co-extruded polyester fibers. The stiffening fibers may be multicomponent binder fibers, where individual fibers are provided from different materials, usually a first and a second polymeric material. The two materials may be chemically different (hence the fibers are chemically heterogeneous) or they may differ only in their physical properties while being chemically identical (hence the fibers are chemically homogeneous). The stiffening fibers may also be a blend of multicomponent fibers with polyester fibers.

With specific reference to multicomponent fibers comprised of a polypropylene/polyethylene fiber composition, in a cross-sectional view of a fiber, the material with a higher softening temperature can provide the central part (i.e., the core) of the fiber. The fiber core typically is responsible for the bicomponent fiber's ability to transmit forces and have a certain rigidity or otherwise provide structures with resiliency. The outer coating on the fiber core (i.e., the sheath) of the fiber can have a lower melting point and may be used to facilitate thermally bonding of substrates comprising such fibers. In one embodiment, a polypropylene core is provided with a polyethylene coating on the outside, such that about 50%, by weight, of the fiber material is polypropylene and 50%, by weight, of the fiber material is polyethylene. Other quantitative amounts can of course be selected. For example, bicomponent fibers can have a composition from about 30% to about 70%, by weight, polyethylene, while others have about 35% to about 65%, by weight polyethylene. In some embodiments, bicomponent fibers can have a composition from about 40% to about 60% or about 45% to about 55%, by weight, polyethylene.

In a preferred embodiment of the present invention, the unitary structure of the fluid distribution layer may be formed as an airlaid material where the at least two sublayers forming it are deposited in subsequent steps on a single airlaid line directly onto the wire carrier and then latex applied to the body facing and garment facing surfaces to ensure proper binding and reduce dustiness.

In each of the processes described above, the sub-layers are formed on an air laid machinery having several forming heads (in general one for each sub layer or that two forming heads could deposit the same composition, thereby forming a single sub-layer) and wherein each forming head lays down a specific combination of materials in a given set of conditions. In this process a first forming head forms a first air laid layer, then a second forming head forms a second air laid sub-layer on top of the first sub-layer. The process goes on until the desired series of sub-layers is obtained. Typically, during the deposition of an air laid layer or sub-layer the composition of the materials (e.g., % of multi-component fibers) deposited by each forming head is constant, however it is possible to envision embodiments where the composition of the materials of each forming head varies. This allows generating a variation of composition and properties of the material along its z axis in a single layer or sub-layer (-z profiling). In the case where more forming heads are present it is possible to conduct gentle compression steps between the passage from one forming head to another, preferably without intermixing of the adjacent sub-layers.

When the deposition of the air laid fluid distribution layer is complete the resulting material may be compressed to compact it (e.g., via calendering). In case multicomponent binder fibers are present, the material can be thermally treated at a temperature above the softening temperature of a bonding component of the multicomponent binder fibers and below the softening point of a structural component in the multicomponent binder fibers so that the binder fibers can bind among sub-layers. The fluid distribution layer may additionally be embossed which may be beneficial for the wet integrity of the fluid distribution layer and to increase its density. The resulting sheet of material can then be cut if necessary in the appropriate size and used within the absorbent core of an absorbent article or combined with another layer to form an absorbent core.

The thickness of the fluid distribution layer may be from 0.25 mm to 5 mm, 0.75 mm to 3.5 mm, 1 mm to 2.5 mm or 1.5 mm to 2 mm. The thickness is determined by the need to balance fluid handling and protection and comfort of the article. For example, if the fluid distribution layer is too thin, it may not be effective to prevent rewet of the article; if the fluid distribution layer is too thick, it may add unnecessary bulk to the absorbent article. In general, for use in menstrual articles, the fluid distribution layer may have a thickness of between 1.8 mm and 4.0 mm; between 2.25 mm and 3.75 mm; between 2.5 mm and 3.5 mm; or between 2.5 mm and 3.0 mm including any values within these ranges and any ranges created thereby. For use in light weight menstrual articles, the fluid distribution layer may have a thickness of from from 0.6 mm to 1.8 mm. When used in articles aiming at handling urine, such as diapers or adult incontinence pads, the fluid distribution layer may have a thickness of between 0.2 mm and 5.0 mm; between 2.25 mm and 3.75 mm; between 2.5 mm and 3.5 mm; or between 2.5 mm and 3.0 mm.

Fluid Storage Layer

The absorbent core further comprises a storage layer 22 containing super absorbent polymers (SAP), such as absorbent gelling materials (AGM) or super absorbent foam materials. The storage layer may comprise from 50%, 60%, 70%, 80% or 90% by weight of the storage layer of super absorbent polymers. The amount of super absorbent polymer material in the fluid storage layer enables the storage layer to draw liquid from the fluid distribution layer, even when the two layers are structurally distinct (i.e., there are no fibers crossing between the layers that would otherwise allow easy transfer of liquid). The fluid storage layer further provides a secure place for exudates to be held when in use.

Absorbent gelling materials (AGM), are typically used in finely dispersed form, e.g. typically in particulate or fiberized form, in order to improve their absorption and retention characteristics. AGM typically comprises water insoluble, water swellable, hydrogel forming crosslinked absorbent polymers which are capable of absorbing large quantities of liquids and of retaining such absorbed liquids under moderate pressure. Absorbent gelling materials can be incorporated in absorbent articles, typically in the absorbent core, in different ways; for example, absorbent gelling materials in particulate form can be dispersed among the fibres of one or more of the fibrous layers comprised in the core, or rather localized in a more concentrated arrangement between fibrous layers so that one or more of the layers making up the core comprise a reduced amount of fibrous materials and/or are essentially made of AGM.

Other examples of AGM according suitable for the present invention are porous super absorbents such as those described in WO 2010118272 A1.

Other examples of SAP suitable for the present invention are foams derived from the polymerization of High Internal Phase Emulsions (Water-in-oil or oil in water emulsions having a high ratio of dispersed aqueous phase to continuous oil phase), also referred to as "HIPE foams". These are formed by polymerizing a High Internal Phase Emulsion comprising an oil phase having monomer, cross-linking agent, emulsifier, photo initiator, and an aqueous phase. Examples of HIPE foams are described in: U.S. Pat. Nos. 5,500,451, 5,817,704, 5,856,366, 5,869,171, 6,369,121, 6,376,565, 6,525,106 and WO 2011081987.

Such superabsorbent HIPE foams are typically cured into layers but can also be used in comminuted form as particles or crumbles which can be applied dispersed into storage layers alone or in combination with absorbent or non absorbent fibers essentially in a similar way to AGM particles.

Absorbent articles according to the present invention may comprise any of the SAPs mentioned above or a mixture thereof.

In some embodiments, portions of the storage layer 22 of the absorbent core can be formed only of SAP, or can be formed of SAP dispersed in a suitable carrier such as cellulose fibers in the form of fluff or stiffened fibers. One example of a non-limiting storage layer comprises AGM particles that may be laminated between liquid permeable layers, such as conventional paper tissue layer (for example, having a basis weight of between 15 g/m² to 20 g/m²), or hydrophilic nonwoven materials, such as those conventionally used for topsheets.

The storage layer may further comprise materials, such as creped cellulose wadding, fluffed cellulose fibers, Rayon fibers, wood pulp fibers also known as airfelt, and synthetic fibers, including cellulose acetate, polyvinyl fluoride, polyvinylidene chloride, acrylics (such as ORLON), polyvinyl acetate, non-soluble polyvinyl alcohol, polyethylene, polypropylene, polyamides (such as nylon), polyesters, bicomponent fibers, tricomponent fibers, mixtures thereof and the like can also be used in the storage layer. The storage layer may also include filler materials, such as PERLITE, diatomaceous earth, VERMICULITE, or other suitable materials that lower rewet problems.

The storage layer may have SAP in a uniform distribution or in a non-uniform distribution. The SAP may be in the form of channels, pockets, stripes, criss-cross patterns, swirls, dots, or any other pattern, either two or three dimensional.

Suitable storage layers may be made in-line during the manufacturing process for absorbent articles with high production speeds of more than 300 m/min or even more than 500 m/min. However, it is often preferred (for process simplicity) that the storage layer materials are provided in a web or sheet form, such that they may be provided pre-formed to a converting unit for making the absorbent articles. In a preferred execution, materials for the storage layer are roll-stock materials, i.e., may be supplied in the form of a web—i.e., essentially a continuous roll or spool. This can reduce the complexity of the manufacturing process by eliminating a complex core forming process step and by reducing additional dust generation.

The Absorbent Core

The absorbent core has a first, upper or body-facing surface and a second, lower or garment facing surface. The body facing surface may be adjacent to the topsheet or may be adjacent an additional layer provided between the topsheet and absorbent core. The garment facing surface of the absorbent core may be adjacent the backsheet. The absorbent core comprises at least a fluid distribution layer that is adjacent to or forms the body facing surface and a fluid storage layer that is adjacent to or forms the garment facing surface. The fluid distribution layer and fluid storage layer are preferably formed as distinct layers that are put together to form the absorbent core. The fluid distribution layer and fluid storage layer may be adhered together by any known means. Given the separate structure and function of the fluid distribution layer and storage layer of the present invention, it is possible to provide a more tailor made absorbent article having a large fluid distribution layer proximal a user's skin and a smaller storage layer distal to the user's skin. The fluid distribution layer is typically soft and cushiony so can provide a great degree of comfort to the user, whereas the storage layer is typically stiffer and denser. There are many variations of how the storage layer may be arranged, but in one example, the storage layer may be positioned directly in the crotch region—this could be for liquid absorption and comfort reasons.

Thus, the storage layer may have a smaller overall surface area than the fluid distribution layer. For example, the storage layer may have a smaller cross direction width, for example extending up to 90% of the width of the fluid distribution layer. Alternatively, the storage layer may have a smaller machine direction length, for example, extending up to 90% of the length of the fluid distribution layer.

In use, the fluid distribution layer will first receive exudates from the body and the capillary flow resulting from the arrangement of different materials of the sub-layers of the fluid distribution layer, will quickly draw the liquid away from the body facing surface of the absorbent article. Due to the high absorption capacity and power of the storage layer, liquid will be drawn from the fluid distribution layer into the storage layer, thus leaving the fluid distribution layer ready to receive subsequent assaults of exudates. In this respect, the SAP present in the storage layers provide a strong suction force to draw liquid out of the fluid distribution layer.

Furthermore, the sub-layers of the fluid distribution layer have been selected and designed such that once the exudates have been drawn into the storage layer, the fluid distribution layer reverts to a cushiony form that is comfortable for the user.

Test Methods

To demonstrate the benefits of the absorbent article of the present invention, exemplary articles incorporating absorbent cores have been evaluated using the following test methods:

The measurements for thickness provided herein were obtained using Worldwide Strategic Partners (WSP) Test Method 120.1 (05) using a 0.25 kPa load.

The measurements for basis weight provided herein were obtained using Worldwide Strategic Partners (WSP) Test Method 130.1.

The measurements for Multiple Strike-Through time and End rewet were obtained by the method described below.

Photographic representations of Stain Perception Measurement Method were obtained by the method described below.

Unless otherwise specified, all tests described herein were conducted on samples conditioned at a temperature of 73° F.±4° F. (about 23° C.±2.2° C.) and a relative humidity of 50%±4% for 2 hours prior to the test.

Multiple Strike-Through & End Rewet

The Multiple Strike-through methods measures the time required for repetitive acquisition of Artificial Menstrual Fluid (AMF) loads onto a test sample. The required time is an indication of the sample's ability to absorb fluid after repeated fluid loads under a given pressure. Acquisition time is measured by using a strike-through plate and an electronic circuit interval timer. The time required for the absorbent article to acquire a dose of AMF is recorded. All measurements are performed in a laboratory maintained at 23° C.±2 C.° and 50%±2% relative humidity.

The rewet method measures the amount of fluid emerging through a repeated wetted topsheet from a wet underlying absorbent structure to cause removable wetness on the topsheet surface. Rewet serves as an estimate of how skin, being in contact with an absorbent structure, could be wetted 5 minutes after the last gush. This method works for fluid amounts of 3×3 ml to simulate an average load on pads. This fluid amounts reflect approx. 90% tile of product loading and the results reflect competitive product performance.

Test liquid AMF preparation: The Artificial Menstrual Fluid (AMF) is composed of a mixture of defibrinated sheep blood, a phosphate buffered saline solution and a mucous component. The AMF is prepared according to the procedure described below such that it has a kinematic viscosity between 7.15 to 8.65 centistokes at 23° C.

Viscosity on the AMF is performed using a low viscosity rotary viscometer (a suitable instrument is the Cannon LV-2020 Rotary Viscometer with UL adapter, Cannon Instrument Co., State College, Pa., or equivalent). The appropriate size spindle for the viscosity range is selected, and the instrument is operated and calibrated as per the manufacturer. Measurements are taken at 23° C.±1 C.° and at 60 rpm. Results are reported to the nearest 0.01 centistokes.

Reagents needed for the AMF preparation include: defibrinated sheep blood with a packed cell volume of 38% or greater (collected under sterile conditions, available from Cleveland Scientific, Inc., Bath, Ohio., or equivalent), gastric mucin with a viscosity target of 3-4 centistokes when prepared as a 2% aqueous solution (crude form, available from Sterilized American Laboratories, Inc., Omaha, Nebr., or equivalent), 10% on a volume per volume basis lactic acid aqueous solution, 10% on a volume per volume basis potassium hydroxide aqueous solution, sodium phosphate dibasic anhydrous (reagent grade), sodium chloride (reagent grade), sodium phosphate monobasic monohydrate (reagent grade) and distilled water, each available from VWR International or equivalent source.

The phosphate buffered saline solution consists of two individually prepared solutions (Solution A and Solution B). To prepare 1 litre of Solution A, add 1.38±0.005 g of sodium phosphate monobasic monohydrate and 8.50±0.005 g of sodium chloride to a 1000 mL volumetric flask and add distilled water to volume. Mix thoroughly. To prepare 1 litre of Solution B, add 1.42±0.005 g of sodium phosphate dibasic anhydrous and 8.50±0.005 g of sodium chloride to a 1000 mL volumetric flask and add distilled water to volume. Mix thoroughly. To prepare the phosphate buffered saline solution, add 450±10 mL of Solution B to a 1000 mL beaker and stir at low speed on a stir plate. Insert a calibrated pH probe (accurate to 0.1 units) into the beaker of Solution B and add enough Solution A, while stirring, to bring the pH to 7.2±0.1.

The mucous component is a mixture of the phosphate buffered saline solution, potassium hydroxide aqueous solution, gastric mucin and lactic acid aqueous solution. The amount of gastric mucin added to the mucous component directly affects the final viscosity of the prepared AMF. To determine the amount of gastric mucin needed to achieve AMF within the target viscosity range (7.15-8.65 centistokes at 23° C.) prepare 3 batches of AMF with varying amounts of gastric mucin in the mucous component, and then interpolate the exact amount needed from a concentration versus viscosity curve with a least squares linear fit through the three points. A successful range of gastric mucin is usually between 38 to 50 grams.

To prepare about 500 ml of the mucous component, add 460±10 mL of the previously prepared phosphate buffered saline solution and 7.5±0.5 mL of the 10% weight per volume potassium hydroxide aqueous solution to a 1000 mL heavy duty glass beaker. Place this beaker onto a stirring hot plate and while stirring, bring the temperature to 45° C.±5 C.°. Weigh the pre-determined amount of gastric mucin (±0.50 g) and slowly sprinkle it, without clumping, into the previously prepared liquid that has been brought to 45° C. Cover the beaker and continue mixing. Over a period of 15 minutes bring the temperature of this mixture to above 50° C. but not to exceed 80° C. Continue heating with gentle stirring for 2.5 hours while maintaining this temperature range. After the 2.5 hours has elapsed, remove the beaker from the hot plate and cool to below 40° C. Next add 1.8±0.2 ml of the 10% v/v lactic acid aqueous solution and mix thoroughly. Autoclave the mucous component mixture at 121° C. for 15 minutes and allow 5 minutes for cool down. Remove the mixture of mucous component from the autoclave and stir until the temperature reaches 23° C.±1 C°.

Allow the temperature of the sheep blood and mucous component to come to 23° C.±1 C°. Using a 500 ml graduated cylinder, measure the volume of the entire batch of the previously prepared mucous component and add it to a 1200 ml beaker. Add an equal volume of sheep blood to the beaker and mix thoroughly. Using the viscosity method previously described, ensure the viscosity of the AMF is between 7.15-8.65 centistokes. If not, the batch is disposed and another batch is made adjusting the mucous component as appropriate.

The qualified AMF should be refrigerated at 4° C. unless intended for immediate use. AMF may be stored in an air-tight container at 4° C. for up to 48 hours after preparation. Prior to testing, the AMF must be brought to 23° C.±1 C°. Any unused portion is discarded after testing is complete.

Referring to FIGS. 3, 4A, 4B, 5A and 5B, the strike-through plate 9001 is constructed of Plexiglas with an overall dimension of 10.2 cm long by 10.2 cm wide by 3.2 cm tall. A longitudinal channel 9007 runs the length of the plate is 13 mm deep, 28 mm wide at the top plane of the plate, with lateral walls that slope downward at 65° to a 15 mm wide base. A central test fluid well 9009 is 26 mm long, 24 mm deep, 38 mm wide at the top plane of the plate with lateral walls that slope downward at 65° to a 15 mm wide base. At the base of the test fluid well 9009, there is an "H" shaped test fluid reservoir 9003 open to the bottom of the plate for the fluid to be introduced onto the underlying article. The test fluid reservoir 9003 has an overall length of 25 mm, width of 15 mm, and depth of 8 mm. The longitudinal legs of the reservoir are 4 mm wide with rounded ends. The central strut has a radius of 3 mm and houses the opposing electrodes 6 mm apart. The lateral sides of the reservoir bow outward at a radius of 14 mm bounded by the overall width of 15 mm. Two wells 9002 (80.5 mm long× 24.5 mm wide×25 mm deep) located outboard of the lateral channel, are filled with lead shot to adjust the overall mass of the plate to provide a constraining pressure of 0.25 psi (17.6 gf/cm2) to the test area. Electrodes 9004 are embedded in the plate 9001, connecting the exterior banana jacks 9006 to the inside wall of the fluid reservoir 9003. A circuit interval timer is plugged into the jacks 9006, and monitors the impedance between the two electrodes 9004, and measures the time from introduction of the AMF into reservoir 9003 until the AMF drains from the reservoir. The timer has a resolution of 0.01 sec.

The test samples may be finished test products that are removed from all packaging using care not to press down or pull on the products while handling. No attempt is made to smooth out wrinkles. The test samples are conditioned at 23° C.±2 C.° and 50%±2% relative humidity for at least 2 hours prior to testing. Alternatively, the test samples may be prepared by positioning an absorbent core underneath a conventional topsheet, such as a 25 g/m2 spun highloft nonwoven made of multicomponent binder fibers, e.g., formed from 2.2 dtex, 4 mm long PE sheath and PET core, or 1.7 dtex PE sheath/PP core, bicomponent fibers. For purposes of the tests described herein, all final test samples used had the same overall dimensions of length (216 mm) and width (62 mm).

The required mass of the strikethrough plate must be calculated for the specific dimensions of the test article such that a confining pressure of 1.72 kPa is applied. Determine the longitudinal and lateral midpoint of the test sample's absorbent core. Measure and record the lateral width of the core to the nearest 0.1 cm. The required mass of the strikethrough plate is calculated as the core width multiplied by strikethrough plate length (10.2 cm) multiplied by 17.6 g/cm2 and recorded to the nearest 0.1 g. Add lead shot to the plate to achieve the calculated mass.

Connect the electronic circuit interval timer to the strikethrough plate 9001 and zero the timer. Place the test product onto a flat, horizontal surface with the body side facing up. Gently place the strikethrough plate 9001 onto the center of the test sample ensuring that the "H" shaped reservoir 9003 is centered over the test area.

Using a mechanical pipette, accurately pipette 3.00 mL±0.05 mL of AMF into the test fluid reservoir 9003. The fluid is dispensed, without splashing, along the molded lip of the bottom of the reservoir 9003 within a period of 3 seconds or less. After the fluid has been acquired, record the acquisition time to the nearest 0.01 second. Thoroughly clean the electrodes 9004 before each test.

Wait five minutes after the end of the fluid acquisition, without removing the plate from the sample. Repeat the measurement twice with the same fluid amount with 5 minutes waiting time between the measurements to reach a total of three repetitive gushes. Write down each single acquisition time.

In like fashion, a total of five (5) replicates samples are tested for each test product to be evaluated. Report the Acquisition Time (sec) as the arithmetic mean of the replicates to the nearest 0.01 sec.

Procedure End Rewet after Multiple Strike-Through:

After the last of three gushes of fluid has been acquired wait another 5 minutes. Prepare seven sheets of filter paper during this time (filter paper—Schleicher & Schuell N° 597, diameter 150 mm, #10311812), ensuring that the filter paper is stored under the same climatic conditions during the test. For each test sample a new stack of filter paper is needed. Take the filter paper by the edge, avoid touching the center. After the 5 minutes waiting time remove the plate and the additional elements from the sample.

Put the test sample under the hydraulic lowering device and place the torn filter paper stack on the test sample. Start the hydraulic lowering device to place the weight (1 psi) and wait 15 seconds.

After the hydraulic lowering device removes the weight, take the stack of filter paper and weigh it to the nearest 0.01 g. Record the weight. Discard used filter paper and tested products. Repeat the procedure for n=5 replicates.

Thickness

The thickness of a layer of the absorbent element structure according to the present invention, as well as of a combinations of layers, for example of an entire absorbent element structure, can be measured with any available method known to the skilled person under the selected confining pressure of 0.25±0.01 psi. For example, the INDA standard test method WSP 120.1 (05) can be used, wherein for the "Thickness testing gage" described under section 5.1, the "applied force", section 5.1.e, is set at 0.25±0.01 psi, and the "Readability", section 5.1.f, has to be 0.01 mm.

Stain Perception Measurement Method

Stain perception is measured by the size of a fluid stain visible on an absorbent article. Artificial menstrual fluid (AMF), as described herein, is dosed onto the surface of an article and is photographed under controlled conditions. The photographic image is then analyzed using image analysis software to obtain measurements of the size of the resulting visible stain. All measurements are performed at constant temperature (23° C.±2 C.° and relative humidity (50%±2%).

The absorbent article sample is cut at the center of the absorbent article with an area of 40×40 mm and along with a calibrated ruler (traceable to NIST or equivalent) is laid horizontally flat on a matte black background inside a light box that provides stable uniform lighting evenly across the entire base of the light box.

A suitable light box is the Sanoto MK50 (Sanoto, Guangdong, China), or equivalent, which provide an illumination of 5500 LUX at a color temperature of 5500K. A Digital Single-Lens Reflex (DSLR) camera with manual setting controls (e.g. a Nikon D40X available from Nikon Inc., Tokyo, Japan, or equivalent) is mounted directly above an opening in the top of the light box so that the entire article and ruler are visible within the camera's field of view.

Using a standard 18% gray card (e.g., Munsell 18% Reflectance (Gray) Neutral Patch/Kodak Gray Card R-27, available from X-Rite; Grand Rapids, Mich., or equivalent) the camera's white balance is custom set for the lighting conditions inside the light box. The camera's manual settings are set so that the image is properly exposed such that there is no signal clipping in any of the color channels. Suitable settings might be an aperture setting of f/11, an ISO setting of 400, and a shutter speed setting of ¹⁄₄₀₀ sec. At a focal length of 35 mm the camera is mounted approximately 14 inches above the article. The image is properly focused, captured, and saved as a JPEG file. The resulting image must contain the entire article and distance scale at a minimum resolution of 15 pixels/mm.

Sample absorbent articles are conditioned at 23° C.±2 C.° and 50%±2% relative humidity for 2 hours prior to testing. Place a sample article flat, with the top sheet of the product facing upward, on the matte surface within the light box along with the ruler. Using a mechanical pipette held approximately 19 mm above the article surface, 2.0 mL 0.05 mL of AMF is slowly and steadily loaded onto the center of the article over a 60 second time period. Images are captured at 60 seconds after the loading.

TABLE 1

Fluid Distribution Layer
Table 1: Formulation of Test Samples

| | Option Number | | | | | |
|---|---|---|---|---|---|---|
| | 1 | | 2 | | 3 | |
| | Option Name | | | | | |
| | Inventive Sample 1 | | Inventive Sample 2 | | Control | |
| | gsm | % | gsm | % | gsm | % |
| Topsheet (NW PP) | 25 | | 25 | | 25 | |
| Formulation of Fluid Distribution Layer (% by weight of fluid distribution layer) | | | | | | |
| First Sub-layer | 60 | 40 | 43.3 | 28.87 | 50.8 | 33.87 |
| Latex (Wacker Airflex 192) | | | 2.5 | 1.7 | 2.5 | 1.7 |
| Untreated Pulp (WY NB416) | 22.5 | 15 | | | 38.7 | 25.8 |
| Multicomponent fibers (including NW carrier layer comprising multicomponent fibers where applicable) (2.2 dtex 4 mm PE/PET) | 37.5 | 25 | 15 | 10 | 9.6 | 6.4 |

TABLE 1-continued

Fluid Distribution Layer
Table 1: Formulation of Test Samples

| | Option Number | | | | | |
|---|---|---|---|---|---|---|
| | 1 | | 2 | | 3 | |
| | Option Name | | | | | |
| | Inventive Sample 1 | | Inventive Sample 2 | | Control | |
| | gsm | % | gsm | % | gsm | % |
| Cross linked cellulose fibers | | | 25.8 | 17.2 | | |
| Second Sub-layer | 90 | 60 | 106.7 | 71.73 | 99.2 | 66.13 |
| Untreated Pulp (WY NB416) | 81.5 | 54.3 | 92.2 | 61.5 | | |
| Treated Pulp (GP4722) | | | | | 77.5 | 51.7 |
| Multicomponent fibers | 6 | 4 | 12 | 8 | 19.2 | 12.8 |
| Latex (Wacker Airflex 192) | 2.5 | 1.7 | 2.5 | 1.7 | 2.5 | 1.7 |
| Total | 150 | 100 | 150 | 100 | 150 | 100 |
| Formulation of Fluid Storage Layer | | | | | | |
| Cellulose Tissue (Sofidel) | 35 | | 35 | | 35 | |
| AGM (Sayiya Transform ex BASF) | 35 | | 35 | | 35 | |
| Backsheet (Polymeric Film) | 12 | | 12 | | 12 | |

Each sample additionally has the same non-woven topsheet and the same 12 gsm polymeric film backsheet. The non-woven topsheet is a 25 g/m² spun high loft non-woven made of polypropylene (PP) fibers with 2% melt additives on the bottom layer.

Note: Table 1 shows the different composition of the different sub-layers of the fluid distribution layer. All % s are by weight of the fluid distribution layer. As described above, the non-woven carrier layer may be formed of 50% to 100% of multicomponent binder fibers. Inventive sample 1 is formed with a non-woven carrier, whereas inventive sample 2 is formed by air-laying the fibers directly onto the carrier wire and subsequently applying latex to bind them. When calculating the % weight by individual sub-layers above, it can be seen that the control features an overall homogenous structure with approximately the same % of multicomponent fibers throughout. By comparison, inventive samples 1 and 2 comprise a greater % of either cross-linked cellulose or multicomponent fibers in the first sub-layer compared with the second sub-layer.

TABLE 2

Multiple Strike-Through and End Rewet measurements

| Sample | IS 1 | IS 2 | Control |
|---|---|---|---|
| Basis Weight (gsm) | 150 | 150 | 150 |
| 1st Acquisition Time (sec) | 21 | 18 | 27 |
| 2nd Acquisition Time (sec) | 50 | 48 | 75 |
| 3rd Acquisition Time (sec) | 89 | 81 | 133 |
| End Rewet (g) | 0.72 | 0.62 | 1.03 |

As can be seen above, the acquisition time for Inventive Samples 1 and 2 is considerably lower than for the Control, even after multiple insults. Furthermore, the end rewet weight is less for Inventive Samples 1 and 2 than the control. This can also be seen for the fluid distribution layer when considered alone—as shown in FIGS. 6A, 6B and 6C.

Figure 6A:
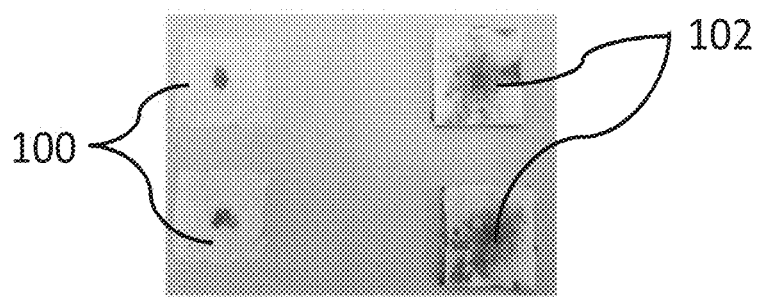
FIG. 6A shows the results of the Stain Size Test conducted on an exemplary topsheet.
Figure 6B:
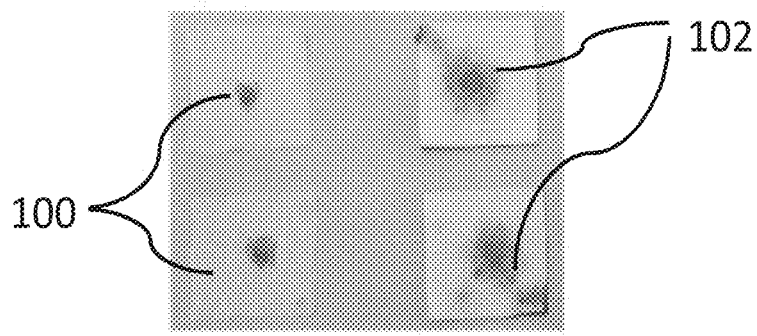
FIG. 6B shows the results of the Stain Size Test conducted on an exemplary fluid distribution layer.
Figure 6C:
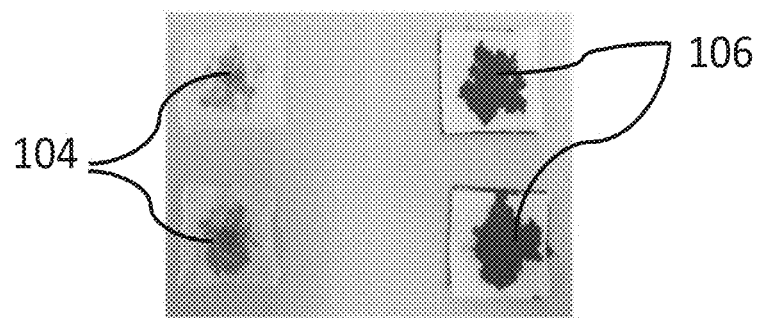
FIG. 6C shows the results of the Stain Size Test conducted on a control topsheet and fluid distribution layer.

FIGS. 6A and 6B show the final stain size on the top surfaces of, respectively, the topsheet 100 and fluid distribution layer 102 for Inventive Samples 1 (FIG. 6A) and Inventive Samples 2 (FIG. 6B). FIG. 6C shows the final stain size on the top surfaces of, respective, the topsheet 104 and fluid distribution layer 106 of the control. As can clearly be seen from these photographs, the stain size is significantly smaller and less intense for Inventive Samples 1 and 2 vs the control.

A. An absorbent article, comprising:
  a) a topsheet;
  b) a backsheet; and
  c) an absorbent core, the absorbent core comprising a fluid distribution layer adjacent the topsheet, the fluid distribution layer being formed of two or more sub-layers comprising:
    i) a first sub-layer proximal to the topsheet, wherein the first sub-layer comprises a first amount of multiple component binder fibers or crosslinked cellulose fibers, or a combination thereof;
    ii) a second and/or subsequent sub-layer distal from the topsheet, wherein the second and/or subsequent sub-layer comprises treated or untreated pulp and a second amount of multiple component binder fibers, crosslinked cellulose fibers, or a combination thereof, wherein the % by weight of the first sub-layer of the first amount of multicomponent binder fibers and/or crosslinked cellulose fibers is greater than the % by weight of the second and/or subsequent sub-layers of the second amount of multicomponent binder fibers and/or crosslinked cellulose fibers; and
  d) a fluid storage layer between the fluid distribution layer and the backsheet, wherein the fluid storage layer comprises at least 50% by weight of the fluid storage layer of a super absorbent polymer.
B. An absorbent article of paragraph B, wherein the first sub-layer further comprises treated or untreated pulp.
C. An absorbent article as described in paragraph A or paragraph B, wherein the fluid distribution layer comprises between 20% to 60% of the first sub-layer by % weight of the fluid distribution layer.
D. An absorbent article as described in any of paragraphs A to C, wherein the first sub-layer comprises between 2% and 30% by weight of the fluid distribution layer of multicomponent binder fibers or crosslinked cellulose fibers.
E. An absorbent article as described in any of paragraphs A to D, wherein the fluid distribution layer comprises one or more additional sub-layers adjacent the second sub-layer and distal to the topsheet, wherein the one or more additional sub-layers comprise the same or less % by weight of the fluid distribution layer of multicomponent binder fibers or crosslinked cellulose fibers.
F. An absorbent article as described in any of paragraphs A to E, wherein the surface area of the fluid storage layer is less than the surface area of the fluid distribution layer.
G. An absorbent article as described in any of paragraphs A to F, wherein the first sub-layer of the fluid distribution layer comprises a non-woven layer that forms the first surface of the fluid distribution layer.
H. An absorbent article as described in any of paragraphs A to G, wherein the fluid distribution layer comprises dispersion binder.
I. An absorbent article as described in any of paragraphs A to H, wherein the first sub-layer of the fluid distribution layer comprises untreated or treated pulp fibers, crosslinked cellulose fibers and multicomponent binder fibers.

J. An absorbent article as described in any of paragraphs A to I, wherein the fluid distribution layer is substantially free of super absorbent polymers.

K. An absorbent article as described in any of paragraphs A to J, wherein said storage layer comprises superabsorbent polymers selected from the group consisting of absorbent gelling material (AGM) or absorbent foam.

L. An absorbent article as described in any of paragraphs A to K, wherein the first sub-layer comprises from 50% to 70% by weight of the first sub-layer of multicomponent binder fibers and from 30% to 50% by weight of the first sub-layer of crosslinked cellulose or pulp fibers and the second sub-layer comprises less than 20% by weight of the second sub-layer of multicomponent binder and/or crosslinked cellulose fibers.

M. An absorbent article as described in any of paragraphs A to K, wherein the first sub-layer comprises from 25% to 100% of crosslinked cellulose fibers and from 5% to 75% by weight of the first sub-layer of multicomponent fibers and the second sub-layer comprises less than 20% by weight of the second sub-layer of multicomponent binder and/or crosslinked cellulose fibers.

This application claims the benefit of EP Application No. 18172398.2, filed on May 15, 2018, the entireties of which are all incorporated by reference herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article, comprising:
   a) a topsheet;
   b) a backsheet; and
   c) an absorbent core, the absorbent core comprising a fluid distribution layer adjacent the topsheet, the fluid distribution layer being formed of two or more sub-layers comprising:
      i) a first sub-layer proximal to the topsheet, wherein the first sub-layer comprises ft from about 30% to about 70% multiple component binder fibers, by weight of the first sub-layer, and from about 50 to about 70% crosslinked cellulose fibers, by weight of the first sub-layer; and
      ii) a second sub-layer distal from the topsheet, wherein the second sub-layer comprises treated or untreated pulp and less than about 20% multiple component binder fibers, by weight of the second sub-layer; and wherein the fluid distribution layer is free of super absorbent polymer; wherein the first sub-layer and second sub-layer comprise a unitary structure;
      iii) a fluid storage layer between the fluid distribution layer and the backsheet, wherein the fluid storage layer comprises at least 50% by weight of the fluid storage layer of a super absorbent polymer wherein the fluid storage layer is free of pulp, wherein the super absorbent polymer is laminated between a tissue layer having a basis weight of 35 $g/m^2$, wherein the surface area of the fluid storage layer is less than the surface area of the fluid distribution layer.

2. An absorbent article as claimed in claim 1, wherein the first sub-layer further comprises treated or untreated pulp.

3. An absorbent article as claimed in claim 1, wherein the fluid distribution layer comprises one or more additional sub-layers adjacent the second sub-layer and distal to the topsheet, wherein the one or more additional sub-layers comprise the same or less % by weight of the fluid distribution layer of multicomponent binder fibers or crosslinked cellulose fibers as the second amount of multicomponent binder fibers or crosslinked cellulose fibers by weight of the second sub-layer.

4. An absorbent article as claimed in claim 1, wherein the first sub-layer of the fluid distribution layer comprises a non-woven layer that forms the first surface of the fluid distribution layer.

5. An absorbent article as claimed in claim 1, wherein the fluid distribution layer comprises dispersion binder.

6. An absorbent article as claimed in claim 1, wherein the fluid storage layer comprises superabsorbent polymers selected from the group consisting of absorbent gelling material or absorbent foam.

7. The absorbent article of claim 1, wherein the multicomponent fibers comprise polyethylene and polyethylene terephthalate.

8. The absorbent article of claim 1, wherein the multicomponent fibers have a fiber size of 2.2 dtex.

9. The absorbent article of claim 1, wherein the fluid distribution layer has a thickness of from about 1.8 mm to about 4.0 mm.

10. An absorbent article, comprising:
    a) a topsheet;
    b) a backsheet; and
    c) an absorbent core, the absorbent core comprising a fluid distribution layer adjacent the topsheet, the fluid distribution layer being formed of two or more sub-layers comprising:
       i) a first sub-layer proximal to the topsheet, wherein the first sub-layer comprises about 34.6% multiple component binder fibers, by weight of the first sub-layer, and about 59.5% crosslinked cellulose fibers, by weight of the first-sub-layer; wherein the multiple component binder fibers comprise polyethylene and polyethylene terephthalate;
       ii) a second sub-layer distal from the topsheet, wherein the second sub-layer comprises about 86.3% treated or untreated pulp and about 11.2% multiple component binder fibers, by weight of the second sub-layer; and wherein the fluid distribution layer is free of super absorbent polymer;

iii) a fluid storage layer between the fluid distribution layer and the backsheet, wherein the fluid storage layer comprises at least 50% by weight of the fluid storage layer of a super absorbent polymer wherein the fluid storage layer is free of pulp, wherein the super absorbent polymer is laminated between a tissue layer having a basis weight of 35 $g/m^2$, wherein the surface area of the fluid storage layer is less than the surface area of the fluid distribution layer.

11. The absorbent article of claim 10, wherein the fluid distribution layer is a unitary structure; wherein the fluid distribution layer comprises a boundary region intermediate the first sub-layer and second sub-layer; wherein the first sub-layer and second sub-layer are intermixed at the boundary region.

* * * * *